United States Patent
Slager et al.

(10) Patent No.: US 11,123,459 B2
(45) Date of Patent: Sep. 21, 2021

(54) HYDROPHOBIC ACTIVE AGENT PARTICLE COATINGS AND METHODS FOR TREATMENT

(71) Applicant: Surmodics, Inc., Eden Prairie, MN (US)

(72) Inventors: Joram Slager, Saint Louis Park, MN (US); Rick Murphy, White Bear Township, MN (US)

(73) Assignee: Surmodics, Inc., Eden Prairie, MN (US)

(*) Notice: Subject to any disclaimer, the term of this patent is extended or adjusted under 35 U.S.C. 154(b) by 96 days.

(21) Appl. No.: 15/842,110

(22) Filed: Dec. 14, 2017

(65) Prior Publication Data

US 2018/0169305 A1 Jun. 21, 2018

Related U.S. Application Data

(60) Provisional application No. 62/435,325, filed on Dec. 16, 2016.

(51) Int. Cl.
*A61L 29/16* (2006.01)
*A61L 29/08* (2006.01)
(Continued)

(52) U.S. Cl.
CPC ............ *A61L 29/16* (2013.01); *A61L 29/085* (2013.01); *A61L 2420/06* (2013.01); *A61L 2420/08* (2013.01); *A61M 25/104* (2013.01); *A61M 2025/105* (2013.01); *C08L 39/06* (2013.01); *C08L 67/04* (2013.01)

(58) Field of Classification Search
None
See application file for complete search history.

(56) References Cited

U.S. PATENT DOCUMENTS

| 4,979,959 A | 12/1990 | Guire |
| 5,002,582 A | 3/1991 | Guire et al. |

(Continued)

FOREIGN PATENT DOCUMENTS

| WO | 2003055611 | 7/2003 |
| WO | 2008/013416 A1 | 1/2008 |

(Continued)

OTHER PUBLICATIONS

Bumbu, G.-G., et al. (2009) "Interpolymer Complexes Containing Copolymers", Chapter 7, p. 173-200, Hydrogen-Bonded Interpolymer Complexes: Formation, Structure, and Applications, World Scientific.

(Continued)

*Primary Examiner* — Kenneth J Stachel
(74) *Attorney, Agent, or Firm* — Kagan Binder, PLLC

(57) ABSTRACT

Drug delivery coatings and devices including the same are described herein. The drug delivery coating has a first coated layer with non-ionic polymer and photogroups, a second coated layer with acid polymer in contact and hydrogen bonded with the first layer, particles with hydrophobic therapeutic agent, and cationic agent. The coating can be provided on a balloon catheter, and the particles and cationic agent can be transferred to tissue during a medical procedure, such as an angioplasty procedure, for a therapeutic effect.

22 Claims, 4 Drawing Sheets

(51) Int. Cl.
   *C08L 39/06* (2006.01)
   *C08L 67/04* (2006.01)
   *A61M 25/10* (2013.01)

(56) References Cited

U.S. PATENT DOCUMENTS

| | | | |
|---|---|---|---|
| 5,061,424 | A | 10/1991 | Karimi et al. |
| 5,263,992 | A | 11/1993 | Guire |
| 5,312,863 | A | 5/1994 | Van Rheenen et al. |
| 5,382,234 | A | 1/1995 | Cornelius et al. |
| 5,414,075 | A | 5/1995 | Swan et al. |
| 5,512,329 | A | 4/1996 | Guire et al. |
| 5,571,089 | A | 11/1996 | Crocker |
| 5,637,460 | A | 6/1997 | Swan et al. |
| 5,714,360 | A | 2/1998 | Swan et al. |
| 5,776,101 | A | 7/1998 | Goy |
| 5,807,331 | A | 9/1998 | Den Heijer et al. |
| 5,858,653 | A | 1/1999 | Duran et al. |
| 5,882,336 | A | 3/1999 | Janacek |
| 6,156,345 | A | 12/2000 | Chudzik et al. |
| 6,394,995 | B1 | 5/2002 | Solar et al. |
| 6,517,515 | B1 | 2/2003 | Eidenschink |
| 6,610,317 | B2 | 8/2003 | Straub et al. |
| 6,623,504 | B2 | 9/2003 | Vrba et al. |
| 7,232,486 | B2 | 6/2007 | Keri et al. |
| 7,772,393 | B2 | 8/2010 | Guire et al. |
| 7,842,312 | B2 | 11/2010 | Burgermeister et al. |
| 8,048,448 | B2 | 11/2011 | Ludwig et al. |
| 8,337,733 | B2 | 12/2012 | Westedt et al. |
| 8,487,137 | B2 | 7/2013 | Guire et al. |
| 8,513,320 | B2 | 8/2013 | Rooijmans |
| 8,585,642 | B2 | 11/2013 | Doshi et al. |
| 8,668,667 | B2 | 3/2014 | Chappa |
| 8,809,411 | B2 | 8/2014 | Rooijmans |
| 8,889,760 | B2 | 11/2014 | Kurdyumov et al. |
| 8,927,000 | B2 | 1/2015 | Chappa et al. |
| 8,951,545 | B2 | 2/2015 | Arps et al. |
| 9,173,974 | B2 | 11/2015 | Gorne et al. |
| 9,321,030 | B2 | 4/2016 | Sukhishvili et al. |
| 9,321,872 | B2 | 4/2016 | Minagawa |
| 9,393,589 | B2 | 7/2016 | Olmeijer et al. |
| 9,439,892 | B2 | 9/2016 | Slager |
| 9,550,011 | B2 | 1/2017 | Xie |
| 2001/0011165 | A1 | 8/2001 | Engelson |
| 2005/0037050 | A1 | 2/2005 | Weber |
| 2006/0169199 | A1 | 8/2006 | Keri et al. |
| 2007/0128731 | A1 | 6/2007 | Deshmukh et al. |
| 2008/0085880 | A1 | 4/2008 | Viswanath et al. |
| 2008/0213334 | A1 | 9/2008 | Lockwood et al. |
| 2008/0213375 | A1 | 9/2008 | Ray et al. |
| 2009/0246262 | A1 | 10/2009 | Arps et al. |
| 2011/0046255 | A1* | 2/2011 | Rooijmans ............ A61L 29/08 522/11 |
| 2011/0059874 | A1 | 3/2011 | Rooijmans |
| 2011/0144373 | A1 | 6/2011 | Swan et al. |
| 2012/0004605 | A1 | 1/2012 | Chappa |
| 2012/0028908 | A1 | 2/2012 | Viswanath et al. |
| 2012/0077049 | A1 | 3/2012 | Lin |
| 2012/0083733 | A1 | 4/2012 | Chappa |
| 2012/0149934 | A1 | 6/2012 | Kurdyumov |
| 2012/0165786 | A1 | 6/2012 | Chappa et al. |
| 2012/0177741 | A1 | 7/2012 | Moslemy |
| 2013/0035483 | A1 | 2/2013 | Zeng et al. |
| 2013/0143056 | A1 | 6/2013 | Swan et al. |
| 2013/0337147 | A1 | 12/2013 | Chappa et al. |
| 2014/0193474 | A1 | 7/2014 | Babcock et al. |
| 2014/0336571 | A1 | 11/2014 | Slager et al. |
| 2015/0017219 | A1 | 1/2015 | Slager et al. |
| 2015/0140107 | A1* | 5/2015 | Slager ............ A61L 29/14 424/497 |
| 2015/0352259 | A1 | 12/2015 | Rooijmans et al. |
| 2016/0053063 | A1 | 2/2016 | Schroter et al. |
| 2016/0175489 | A1 | 6/2016 | Babcock et al. |
| 2016/0310643 | A1 | 10/2016 | Dias et al. |
| 2017/0281557 | A1 | 10/2017 | Slager |

FOREIGN PATENT DOCUMENTS

| | | |
|---|---|---|
| WO | 2008/014222 A1 | 1/2008 |
| WO | 2008104573 | 9/2008 |
| WO | 2011123441 | 10/2011 |
| WO | 2011123730 A1 | 10/2011 |
| WO | 2012/026896 A1 | 3/2012 |
| WO | 2012/101455 A1 | 8/2012 |
| WO | 2016123480 A1 | 8/2016 |

OTHER PUBLICATIONS

Khutoryansky, V.V., et al.,"pH- and Ionic Strength Effects on Interpolymer Complexation Via Hydrogen-Bonding", Chapter 1, p. 1-5, Hydrogen-Bonded Interpolymer Complexes:Formation, Structure, and Applications; World Scientific. (2009).

Love et al., (2010) "Lipid-like Materials for Low-Dose, in Vivo Gene Silencing",PNAS, 107(5),1864-1869.

Hornedo et al., (1999) "Significance of Controlling Crystallization Mechanisms and Kinetics in Pharmaceutical Systems", Pharmaceutical Sciences 88(7), 651-660.

Murdock, R.C. et al. (2008) "Characterization of Nanomaterial Dispersion in Solution Prior to In Vitro Exposure Using Dynamic Light Scattering Technique", Toxicological Sciences 101(2), 239-253.

Wen et al. (2007), "Effects of Polyethylenimine on the Dispersibility of Hollow Silica Nanoparticles", Front. Chem. Eng. China 1:277-282.

Kohler, U., et al., (2008) "Investigations on non-Spherical Reference Material Using Laser Diffraction and Dynamic Image Analysis", Particulate Systems Analysis, 1-5.

https://www.sympatec.com/EN/ImageAnalysis/Fundamentals.html, "Fundamentals—Particle Size and Shape Calculation by Image Analysis", Sympatec GmbH System-Partikel-Technik; retrieved Jan. 6, 2016 6 pages.

* cited by examiner

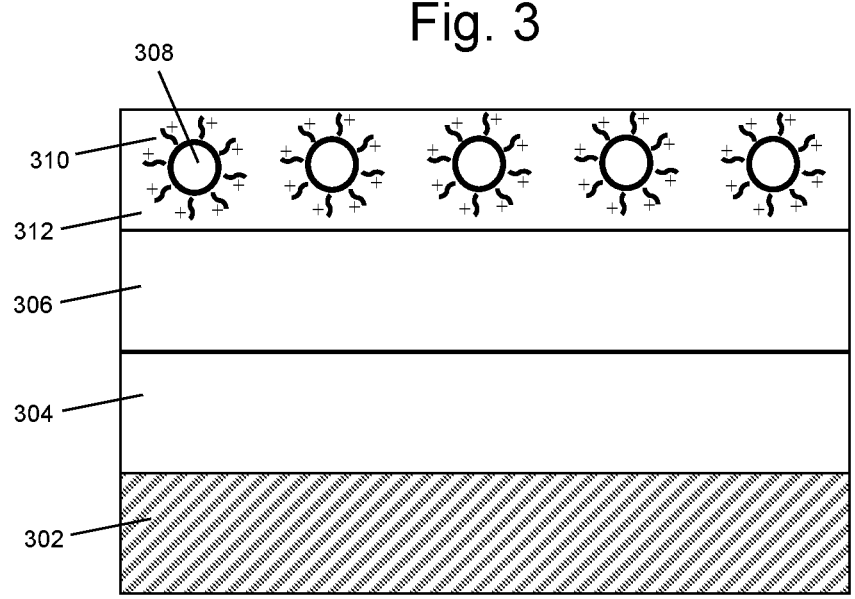
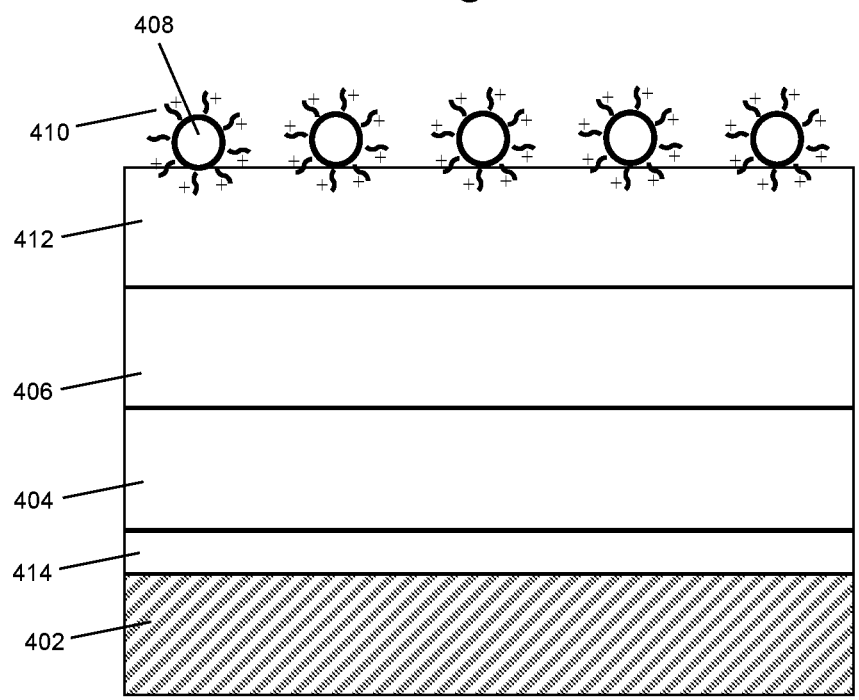

HYDROPHOBIC ACTIVE AGENT PARTICLE COATINGS AND METHODS FOR TREATMENT

CROSS-REFERENCE TO RELATED APPLICATION

This application claims the benefit under 35 USC § 119(e) of U.S. Provisional Patent Application No. 62/435,325, filed Dec. 16, 2016, which is incorporated herein by reference in its entirety.

FIELD OF THE INVENTION

The present invention relates to devices and coatings for devices such as medical device. More specifically, the present invention relates to devices and coatings for devices including hydrophobic active agent particles.

BACKGROUND OF THE INVENTION

The vascular system of the human is subject to blockage due to plaque within the arteries. Partial and even complete blockage of arteries by the formation of an atherosclerotic plaque is a well-known and frequent medical problem. Frequently, such blockage occurs in the coronary arteries. Blockages may also occur secondary to past treatment of specific sites and be associated with restenosis, stemming from rapidly dividing smooth muscle cells. In addition, blockages can also occur in the context of peripheral arteries.

Blockages may be treated using atherectomy devices, which mechanically remove the plaque; hot or cold lasers, which vaporize the plaque; stents, which hold the artery open; and other devices and procedures designed to increase blood flow through the artery.

One common procedure for the treatment of blocked arteries is percutaneous transluminal coronary angioplasty (PTCA), also referred to as balloon angioplasty. In this procedure, a catheter having an inflatable balloon at its distal end is introduced into the coronary artery, the deflated, folded balloon is positioned at the stenotic site, and then the balloon is inflated. Inflation of the balloon disrupts and flattens the plaque against the arterial wall, and stretches the arterial wall, resulting in enlargement of the intraluminal passageway and increased blood flow. After such expansion, the balloon is deflated, and the balloon catheter removed. A similar procedure, called percutaneous transluminal angioplasty (PTA), is used in arteries other than coronary arteries in the vascular system. In other related procedures, a small mesh tube, referred to as a stent is implanted at the stenotic site to help maintain patency of the coronary artery. In rotoblation procedures, also called percutaneous transluminal rotational atherectomy (PCRA), a small, diamond-tipped, drill-like device is inserted into the affected artery by a catheterization procedure to remove fatty deposits or plaque. In a cutting balloon procedure, a balloon catheter with small blades is inflated to position the blades, score the plaque, and compress the fatty matter into the artery wall. During one or more of these procedures, it may be desirable to deliver a therapeutic agent or drug to the area where the treatment is occurring to prevent restenosis, repair vessel dissections or small aneurysms or provide other desired therapy.

Additionally, it may be desirable to transfer therapeutic agents to other locations in a mammal, such as the skin, neurovasculature, nasal, oral, the lungs, the mucosa, sinus, the GI tract or the renal peripheral vasculature.

SUMMARY OF THE INVENTION

Embodiments of the invention include devices having drug delivery coatings, methods for preparing the device coatings, and methods for treating a patient using the coated devices. The inventive coatings can be used to deliver a therapeutic agent in particle form to a target site in a patient, where the therapeutic agent is released at the target site to provide a therapeutic effect to the patient. The coated device can be a component of a medical device system.

In an embodiment, the invention provides a device having a drug delivery coating. The coating includes (a) a first coated layer including (a1) a non-ionic polymer having one or more chemical groups selected from the group consisting of amides, ethers, and alcohols. The first coated layer also includes (a2) photoreactive groups. The photoreactive groups can be pendent from the non-ionic polymer, pendent from a cross-linking agent, or both. If a crosslinking agent is used it has at least two photoreactive groups. The coating also includes (b) a second coated layer that is in direct contact with the first coated layer and which includes an acid polymer. The first coated layer is between the second coated layer and a device surface. The coating also includes (c) a particle comprising a hydrophobic therapeutic agent; and (d) a cationic agent, wherein the cationic agent is associated with the particle. The particle is within the second coated layer, associated with an outer surface of the second coated layer, or indirectly associated with the second coated layer.

Hydrogen bonding can exist between materials of the first and second coated layer to provide improved coating properties. For example, the amide, ether, and/or alcohol group of the non-ionic polymer can hydrogen bond to the acid group of the acid polymer of the second coated layer. Exemplary hydrogen bonding polymers of the first and second coated layers are a vinyl pyrrolidone polymer, and an acrylic acid polymer, respectively. The photoreactive groups, such as present as a pendent group from the non-ionic polymer, present on a photo-crosslinker, can also improve coating properties. The improved properties can be one or more of improved durability, improved compliance, low friction, and reduced particulates that are other than the therapeutic agent particles (i.e., non-therapeutic agent, non-degradable particulates).

The therapeutic agent particle can include a therapeutic such as a macrolide, like rapamycin, or a taxane, such as paclitaxel, that can provide a therapeutic effect to diseased arteries to reduce atherosclerotic stenosis or to recanalize occluded arteries. The cationic agent, such as a cationic lipids or cationic polymers, can promote improved therapeutic agent release from the coating. The cationic agent may also exhibit affinity for the surface of a cell membrane.

In another embodiment, the invention provides a balloon catheter with therapeutic agent coating. The balloon catheter can include a balloon portion comprising (a) a first coated layer with a non-ionic polymer and photoreactive groups; (b) a second coated layer with an acid polymer; (c) a particle with hydrophobic therapeutic agent; and (d) a cationic agent. The balloon catheter can also include a catheter shaft comprising a lubricious coating. In some embodiments, the lubricious coating is formed from the same acid polymer that is used to form the second layer of the drug delivery coating. Beneficially, in addition to the lubricity, durability, and low friction properties that the polymers of the first and second coated layers provide, these polymers also provide an excellent surface on which the particles of hydrophobic therapeutic agent and cationic agent can be disposed.

In another embodiment, the invention provides a method for providing a therapeutic agent to a subject. In the method the coated device including (a) the first coated layer with non-ionic polymer and photoreactive groups; (b) the second coated layer with acid polymer; (c) the particle with hydrophobic therapeutic agent; and (d) the cationic agent, as described herein, is introduced into a patient so that the therapeutic agent is released to the patient to provide a therapeutic effect. In some embodiments, the drug delivery coating is formed on a balloon surface of a balloon catheter and the therapeutic agent is released to the patient by expanding the balloon at a target location in the patient. In the method at least a portion of the particles including therapeutic agent become disassociated from the coating and released into the patient. In association with procedures such as percutaneous transluminal coronary angioplasty (PTCA), percutaneous transluminal angioplasty (PTA), and the like, the therapeutic agent delivered to the treatment area can prevent restenosis, repair vessel dissections or small aneurysms, or provide other desired therapy.

In another embodiment, the invention provides a method for forming a drug delivery coating. In the method a composition including the non-ionic polymer and photoreactive groups as described herein, is disposed on a device surface to form a first coated layer. Next, the first coated layer may be treated with UV irradiation, or this step can be performed after the material for the second coated layer is deposited. Next, a composition comprising an acid polymer is disposed on the first coated layer. The composition with the acid polymer can optionally include a particle with hydrophobic therapeutic agent and cationic agent. Alternatively, after the second coated layer is formed a step of applying a composition that includes a particle with a hydrophobic therapeutic agent and cationic agent is performed. The particular becomes associated with an outer surface of the second coated layer, or becomes indirectly associated with the second coated layer, such as if the composition includes another polymer and the particle becomes present in an optional third polymeric layer.

In another embodiment, the coated device is a component of a medical system or kit. For example, the system or kit can include an insertion tool for introducing the balloon catheter in the body.

The drug delivery coatings of the invention provide or more of the following advantages for use in the body: maintaining structural integrity during steps associated with preparation of the balloon catheter device include pleating, folding, and curing (such as heat treatment); maintaining structural integrity during the process of passing through the vasculature through a catheter and/or over the guide wire, with limited loss of the active agent; transfer of a substantial amount of the active agent from the balloon and onto the vessel wall; maximization of uptake of the active agent into the tissue of the vessel wall and reduction in the amount of active agent that is washed away into the blood flowing through the treatment site in the vasculature.

BRIEF DESCRIPTION OF THE FIGURES

FIG. 3 is a cross-sectional illustration of a drug delivery coating.

FIG. 4 is a cross-sectional illustration of a drug delivery coating.

DETAILED DESCRIPTION OF THE INVENTION

Figure 1:
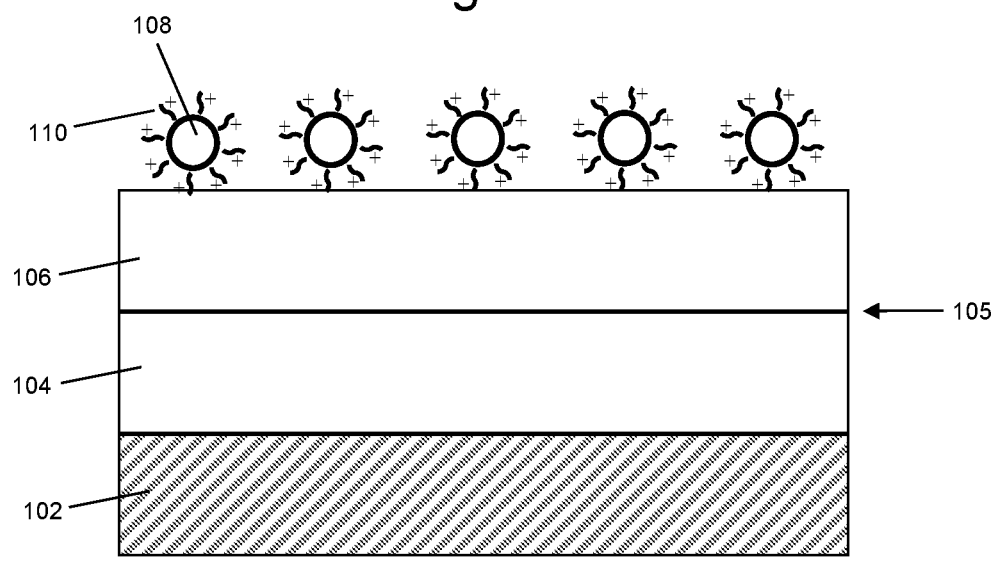
FIG. 1 is a cross-sectional illustration of a drug delivery coating.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As discussed herein, the disclosure includes description of devices having drug delivery coatings, methods for preparing the device coatings, and methods for treating a patient using the coated devices. Exemplary devices are medical devices that can be inserted or implanted in the body, wherein the drug deliver coating is placed in proximity to a tissue that is desired to receive the therapeutic agent.

The coating can be formed on the surface of an insertable or implantable medical device. An "insertable" medical article can be one that is introduced into a mammal for the prophylaxis or treatment of a medical condition and can be used for short term use, or, less frequently, longer term treatment. An "implantable" medical article can more specifically refer to those insertable medical intended for longer term insertion (i.e., placement) at a target site in the body, such a period of days, weeks, or months.

The medical device can be made from one or more "device materials" on which the coating can be formed. In some embodiments the medical device is made partially or entirely fabricated from a plastic polymer. Plastic polymers include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides (e.g., PEBAX), polysulfones, poly(ethylene terephthalate), polydimethylsiloxanes, and polyetherketone.

In some embodiments the medical device is made from a material including a metal. Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

Various types of medical devices can include a drug delivery coating according to the current disclosure, such as drug eluting balloon catheters, drug-containing balloon catheters, stents, grafts, and the like. Some embodiments described herein can be used in conjunction with balloon expandable flow diverters, and self-expanding flow diverters. Other embodiments can include uses in contact with angioplasty balloons (for example, but not limited to, percutaneous transluminal coronary angioplasty and percutaneous transluminal angioplasty). Yet other embodiments can include uses in conjunction with sinoplasty balloons for ENT treatments, urethral balloons and urethral stents for urological treatments and gastro-intestinal treatments (for example, devices used for colonoscopy). Hydrophobic active agent can be transferred to tissue from a balloon-like inflatable device or from a patch-like device. Other embodiments of the present disclosure can further be used in conjunction with micro-infusion catheter devices. In some embodiments, micro-infusion catheter devices can be used to target active agents to the renal sympathetic nerves to treat, for example, hypertension.

Embodiments included herein can also be used in conjunction with the application of various active agents to the skin (for example, but not limited to transdermal drug delivery).

Other exemplary medical applications wherein embodiments of the present disclosure can be used further encompass treatments for bladder neck stenosis (e.g. subsequent to transurethral resection of the prostrate), laryngotrachial stenosis (e.g. in conjunction with serial endoscopic dilatation to treat subglottic stenosis, treatment of oral cancers and cold sores and bile duct stenosis (e.g. subsequent to pancreatic, hepatocellular of bile duct cancer). By way of further example, embodiments herein can be used in conjunction with drug applicators. Drug applicators can include those for use with various procedures, including surgical procedures, wherein active agents need to be applied to specific tissue locations. Examples can include, but are not limited to, drug applicators that can be used in orthopedic surgery in order to apply active agents to specific surfaces of bone, cartilage, ligaments, or other tissue through physical contact of the drug applicator with those tissues. Drug applicators can include, without limitation, hand-held drug applicators, drug patches, drug stamps, drug application disks, and the like.

In some embodiments coatings of the present disclosure can be used on a catheter. Exemplary catheters include balloon catheters, central venous access catheters, vascular access catheters, intravenous catheters, stroke therapy catheters, blood pressure and stent graft catheters, Foley catheters, urethral catheters, PTCA atherectomy catheters, ablation catheters, cardiac catheters, angiography catheters, peripheral catheters, and wound drainage catheters.

Of particular relevance are balloon catheters. For example, the drug delivery coating can be formed on an expandable (e.g., balloon) surface of a balloon catheter. The balloon catheter can be inserted into a patient to place the expandable elastic surface of the balloon portion in contact with a target tissue to which the particles can be transferred. The balloon can be expanded, causing release or dissociation of the particles from drug delivery coating. Balloon catheters are commonly used in angioplasty procedures for the treatment of arteries that are diseased. Balloon angioplasty generally involves the dilation or reopening of blocked intraluminal channels. Aspects of the disclosure wherein a drug delivery coating is formed on a balloon catheter will be discussed in greater detail herein.

The balloon of a balloon catheter is typically formed from a material, or combination of materials, capable of expanding, and suitable for use within the body. Expandable elastic materials are compliant and flexible materials, such as elastomers (polymers with elastic properties), which are typically thermoplastic polymers. Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, and polyether-polyamide copolymers.

Exemplary thicknesses for the walls of catheter balloons are in the range of about 5 µm to about 20 µm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon. In some cases, a balloon with a thin wall is used, so as to accommodate the increase in thickness when a drug delivery coating is formed on the surface. The manufacture of expandable elastic substrates is well known in the art, and any suitable process can be carried out to provide the expandable substrate portion of the insertable medical device as described herein. Catheter balloon construction is described in various references, for example, U.S. Pat. Nos. 4,490,421, 5,556,383, 6,210,364, 6,168,748, 6,328,710, and 6,482,348. Molding processes are typically performed for balloon construction.

As a general matter, the drug delivery coating includes a first coated layer with a non-ionic polymer and photoreactive groups, a second coated layer that is in direct contact with the first coated layer and which includes an acid polymer, and a particle comprising a hydrophobic therapeutic agent and a cationic agent, wherein the cationic agent is associated with the particle. The arrangement of the coating layers can optionally be described with regards to their spatial relationship to the device surface. For example, relative to second coated layer, the first coated layer will be proximal to the device surface. For example, relative to first coated layer, the particles with cationic agent will be distal to the device surface.

The coating can optionally include one or more additional coated layers (e.g., a third, fourth, fifth coated layer, etc.). For example, the coating may further include one or more additional coated layer(s) between the first coated layer and the device surface, or more additional coated layer(s) on top of the second coated layer (e.g., as an outer coating), or combinations thereof. An optional additional coated layer between the first coated layer and the device surface may be referred to as a "primer layer" (or "tie layer" or third coated layer) if in direct contact with the material of the device surface. Depending on the type of device material (e.g., plastic, metal, etc.) the drug delivery coating is formed, on an optional primer layer may facilitate formation of the first coated layer that includes the non-ionic polymer and photoreactive groups. The primer layer can also provide a target material for the bonding of photoreactive groups. Exemplary tie layers include, but are not limited to silane-containing compounds, such as hydroxy- or chloro-silane, butadiene, polyurethane, and Parylene™. A Parylene™ (poly(paraxylylene) layer can be vapor deposition polymerization (VDP), such as described in U.S. Publication No. 2005/0244453 (Nov. 3, 2005; Stucke et al.). Silane tie layers are described in US Patent Publication 2012/0148852 (Jelle, et al.).

The coating can optionally include one or more additional optional coated layers that are distal to (e.g., on top of) the second coated layer with the acid polymer. For example, an optional coated layer can be in contact with the second coated layer and can provide benefits for the delivery of the therapeutic agent particle, or can protect the particle prior to the therapeutic agent being released to tissue. If a third coated layer in contact with the second coated layer is present, the therapeutic agent particle can be located within the third coated layer, the therapeutic agent particle can be between the second and third coated layer, or the therapeutic agent particle can be associated with the surface of the third coated layer. An optional third coated layer can be less stable than the first and second coated layer. For example, an optional third layer can include one or more biodegradable materials, or biocompatible materials that loosens from the drug coating and is partially or fully removed during the drug delivery method.

Exemplary coating arrangements are shown in FIGS. 1-4.

FIG. 1 is a schematic cross-sectional illustration of a drug delivery coating embodiment of the disclosure. In this embodiment, the first layer 104 which includes the non-ionic polymer and the photoactive groups is in direct contact with a device surface 102, such as an elastomeric surface of a balloon portion of a balloon catheter. The second layer 106 is in direct contact with the first layer 104. At the interface 105 between the first coated layer 104 and second layer 106, hydrogen bonding between groups of the non-ionic polymer and the acid polymer can be present. In some aspects, there may be covalent bonding between the photoreactive groups of the first layer 104 and material of the device surface 102. Therapeutic agent particles 108 with cationic agent 110 disposed over particle 108 are associated with the surface of the second layer 106. The charge provided by the cationic agents 110 can be electrostatically attracted to negative charges and/or polar groups associated with the target tissue (not shown), such as the lipid bilayer of a cell membrane and cellular components within the lipid bilayer. The electrostatic attraction can promote the movement of the therapeutic agent particles 108 away from the surface of the second layer 106 and to tissue.

Figure 2:
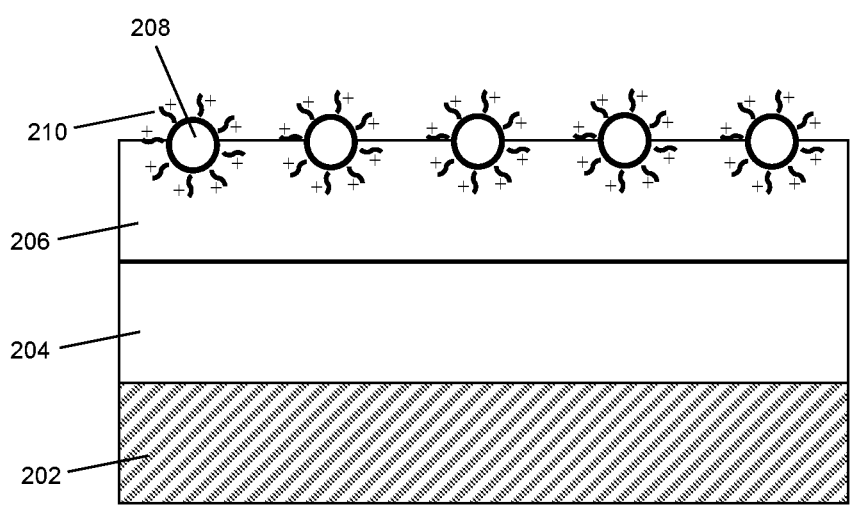
FIG. 2 is a cross-sectional illustration of a drug delivery coating.

FIG. 2 is a schematic cross-sectional illustration of another drug delivery coating embodiment of the disclosure. In this embodiment, the first layer 204 is in direct contact with a device surface 202 and the second layer 206 is in direct contact with the first layer 204. Hydrogen bonding and, optionally, photogroup bonding can be present in this coating embodiment, such as described with reference to FIG. 1. Therapeutic agent particles 208 with cationic agent 210 disposed over particle 208 are at least partially embedded in the second layer 206. The second layer 206 can be prepared in a way so that the at least partially embedded particles 208 are releasable from the second coated layer.

FIG. 3 is a schematic cross-sectional illustration of another drug delivery coating embodiment of the disclosure. In this embodiment, the first layer 304 is in direct contact with a device surface 302 and the second layer 306 is in direct contact with the first layer 304. Hydrogen bonding and, optionally, photogroup bonding can be present in this coating embodiment, such as described with reference to FIG. 1. The coating includes a third layer 312 that is in contact with the second layer 306. Therapeutic agent particles 308 with cationic agent 310 disposed over particle 308 are within the third layer 312. The third layer 312 can be different from the first and second layers, and can be formed at least partially from a material that is less stable than the polymers of the first and second coated layers, such as a biodegradable polymer or a lipid. In use, the material of the third layer 312 can biodegrade, loosen, or be removed from the coating, or combinations thereof, so the particles 308 can be released and move to target tissue through electrostatic attraction.

FIG. 4 is a schematic cross-sectional illustration of another drug delivery coating embodiment of the disclosure. In this embodiment, the coating includes a primer layer 414 that is in contact with a device surface 402. The first layer 404 which is then in direct contact with the primer layer 414 and optionally there can be covalent bonding between the photogroups of the first layer 404 and the primer layer 414. The second layer 406 is in direct contact with the first layer 404, and hydrogen bonding can be present between these two layers, such as described with reference to FIG. 1. The coating includes a third layer 412 that is in contact with the second layer 406. Therapeutic agent particles 408 with cationic agent 410 disposed over particle 408 are on the surface or partially embedded within the third layer 412. The third layer 312 can have properties as described with reference to FIG. 3, or can be of a different material. The particles 408 can be dislodged from the third layer 412, or the material of the third layer 412 can biodegrade, loosen, or be removed from the coating, or combinations thereof, so the particles 408 can be released and move to target tissue through electrostatic attraction.

Figure 5:
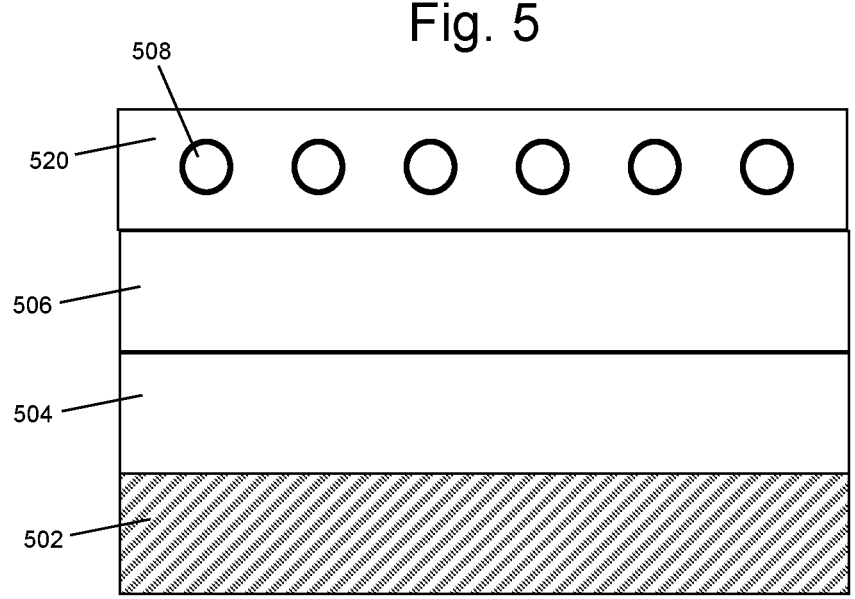
FIG. 5 is a cross-sectional illustration of a drug delivery coating.

FIG. 5 is a schematic cross-sectional illustration of another drug delivery coating embodiment of the disclosure. In this embodiment, the first layer 504 which is in direct contact with a device surface 502 and the second layer 506 is in direct contact with the first layer 504. Hydrogen bonding and, optionally, photogroup bonding can be present in this coating embodiment, such as described with reference to FIG. 1. The coating includes a third layer 520 that is in contact with the second layer 506. The third layer 520 includes partially or fully a cationic agent that otherwise is disposed on the particles in the embodiments of FIGS. 1-4. In use, the third layer 520 containing cationic agent can separate from the second layer 506, and affect movement of the particles 508 away from the coating and to target tissue through electrostatic attraction.

The first layer (e.g., 104, 204, 304, 404, 504) can include one or more non-ionic polymer(s) that can undergo hydrogen bonding with an acid polymer of the second layer (e.g., 106, 206, 306, 406, 506). Chemical groups of the non-ionic polymer that can undergo hydrogen bonding include amide, ether, and hydroxyl chemical groups. Preferred amide groups include tertiary amide groups and lactam groups. Such chemical groups can be spaced away from the chemical backbone.

Examples of polymers that include such chemical groups include those formed from monomers such as N-vinyl caprolactam, N-vinyl pyrrolidone, ethylene oxide, propylene oxide, propylene glycol, vinyl methyl ether, acrylamide, N-isopropylacrylamide, N, N-dimethylacrylamide, vinyl alcohol, 2-hydroxyethylacrylate, 2-hydroxyethyl vinyl ether, 2-ethyl-2-oxazoline, n-acetyliminoethylene, and n-glucose. Polymers formed from such monomers, but are not limited to, lactam containing polymers such as poly(N-vinyl caprolactam) and poly-(vinyl pyrrolidone); ether-containing polymers such as poly(ethylene oxide) (PEO), poly(propylene oxide) (PPO), poly(propylene glycol) (PPG) poly(vinyl methyl ether), or blends or copolymers thereof; non-ionic acrylic type polymers such as polyacrylamide, poly(N-isopropylacrylamide), and poly(N,N-dimethylacrylamide); polymeric alcohols such as poly(vinyl alcohol) (PVA), poly (2-hydroxyethylacrylate) (PHEA) and poly(2-hydroxyethyl vinyl ether) PHEVE), poly(2-ethyl-2-oxazoline) (PEOX), poly(n-acetyliminoethylene) (PAIE) and water soluble polysaccharides such s methyl cellulose, hydroxypropylcellulose and hydroxyethylcellulose. (see "Hydrogen-Bonded Interpolymer Complexes; Formation, Structure and Applications" Chapters 1 and 7, Eds. Vitaliy V. Khutoryanskiy and Georgios Stalkos (2009).

In some embodiments, coating has a first layer that includes a vinyl pyrrolidone polymer. As used herein a "vinyl pyrrolidone polymer" refers to polymers including vinyl pyrrolidone monomeric units. The vinyl pyrrolidone polymer can be a vinyl pyrrolidone homopolymer or a vinyl pyrrolidone copolymer including vinyl pyrrolidone and one or more (e.g., two, three, four, five, etc.) other monomeric units that are different than vinyl pyrrolidone. In embodiments, in a poly(vinyl pyrrolidone) copolymer, the vinyl pyrrolidone can be the primary monomer (molar quantity), such as present in an amount of greater than 50% (mol), 60% (mol) or greater, 70% (mol) or greater, 80% (mol) or greater, 90% (mol) or greater, 95% (mol) or greater, 97.5% (mol) or 99% (mol) or greater. In exemplary embodiments, vinyl pyrrolidone is present in the copolymer in the range of about 75% (mol) to about 97.5% (mol), or about 90% (mol) to about 97.5% (mol).

Other monomers that can be copolymerized with vinyl pyrrolidone to provide the vinyl pyrrolidone polymer include, but are not limited to acrylamide, methacrylamide, methyl acrylate, methyl methacrylate, hydroxyethyl methacrylate, hydroxyethyl acrylate, glyceryl acrylate, glyceryl methacrylate, ethylene glycol, and derivatives of these monomers.

The first coated layer also includes photogroups, and these can be present, in embodiments, as pendent groups from the non-ionic polymer backbone. For example, in some embodiments, the first coated layer includes a vinyl pyrrolidone polymer comprising a photoreactive group (e.g., photo-PVP). Reagents and methods for the preparation of photo-PVP can be found in references such as U.S. Pat. Nos. 4,979,959; 5,002,582; 5,263,992; 5,414,075; 5,512,329; and 5,637,460, the teaching of which are incorporated herein by reference. In some modes of practice, photo-PVP can be formed by the copolymerization of 1-vinyl-2-pyrrolidone and N-(3-aminopropyl (meth)acrylamide), which then can be derivatized with an acyl chloride (such as, for example, 4-benzoylbenzoyl chloride) under Schotten-Baumann conditions. That is, the acyl chloride reacts with the amino group of the N-(3-aminopropyl) moiety of the copolymer. An amide is formed resulting in the attachment of the aryl ketone to the polymer.

A vinyl pyrrolidone polymer comprising a photoreactive group can also be prepared by copolymerizing vinyl pyrrolidone with a monomer derivatized with a photoreactive group. Exemplary monomer derivatives include aryl ketone derivatives of hydrophilic free radically polymerizable monomers such as acrylamide, methacrylamide and AMPS. One exemplary methacrylamide-based monomer with a pendent photoreactive groups is N-[3-(4-benzoylbenzamido) propyl]methacrylamide (BBA-APMA), the synthesis which is described in Examples 1-3 of U.S. Pat. No. 5,858,653 (Duran et al.) Another exemplary methacrylamide-based monomer with a pendent photoreactive group is N-[3-(7-methyl-9-oxothioxanthene-3-carboxiamido)propyl]methacrylamide (MTA-APMA), the synthesis which is described in Examples 1-2 of U.S. Pat. No. 6,156,345 (Chudzik et al.)

In embodiments, the one or more non-ionic polymer(s) that can undergo hydrogen bonding with an acid polymer of the second layer can be the predominant polymer(s) in the first coated layer (>50% wt of the total polymeric content of the first coated layer). Preferably, the non-ionic polymer(s) is 75% wt or greater, 85% wt or greater, 90% wt or greater, 95% wt or greater, or 98% wt or greater, of the total polymeric content of the first coated layer. For example, the non-ionic polymer is present in an amount in the range of about 50% wt to 100% wt, or 90% wt to 100% wt, of the total polymeric content of the first coated layer.

The first coated layer includes photoreactive groups, which may be present pendent from the non-ionic polymer, present on a crosslinking agent, or both. Exemplary crosslinking agents comprising at least two photoreactive groups are described in greater detail herein. Within the first coated layer, the components can be homogenously mixed in some embodiments.

Optionally, the coating can include a crosslinking agent. A crosslinking agent can promote the association of polymers in the coating, or the bonding of polymers to the coated surface. The choice of a particular crosslinking agent can depend on the ingredients of the coating composition.

Suitable crosslinking agents can include two or more activatable groups, which can react with the polymers in the composition. Suitable activatable groups can include photoreactive groups as described herein, like aryl ketones, such as acetophenone, benzophenone, anthraquinone, anthrone, quinone, and anthrone-like heterocycles. A crosslinking agent including a photoreactive group can be referred to as a photo-crosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenyl-methyleneoxy) benzene-1,3-disulfonic acid or salt; 2,5-bis(4-benzoylphenylmethyleneoxy) benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyl dimethylammonium) dibromide and the like. See U.S. Pat. No. 5,714,360 (Swan et al.) the disclosures of which are incorporated herein by reference.

In yet other embodiments, restrained multifunctional reagents with photoactivable crosslinking groups can be used. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Additional crosslinking agents can include those having formula Photo1-LG-Photo2, wherein Photo1 and Photo2 independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

In some embodiments, the crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, the crosslinking agents comprises a linking agent having formula Photo1-LG-Photo2, wherein Photo1 and Photo2, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, the crosslinking agent comprises a linking agent having a formula selected from:

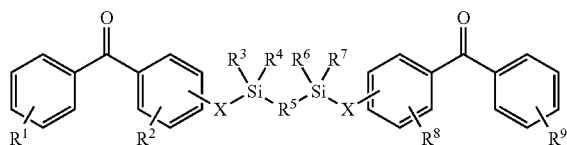

(a)

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

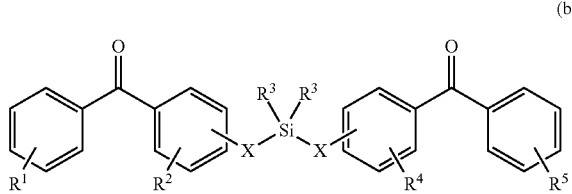

(b)

wherein R1 and R5 are any substitution; R2 and R4 can be any substitution, except OH; R3 can be alkyl, aryl, or a combination thereof; and X, independently, are O, N, Se, S, alkylene, or a combination thereof;

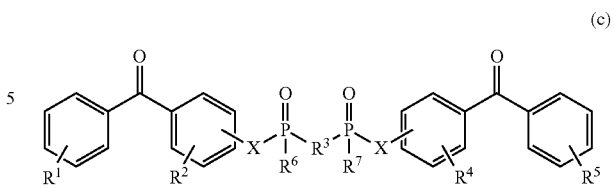

(c)

wherein R1, R2, R4 and R5 are any substitution; R3 is any substitution; R6 and R7 are alkyl, aryl, or a combination thereof; and each X can independently be O, N, Se, S, alkylene, or a combination thereof; and

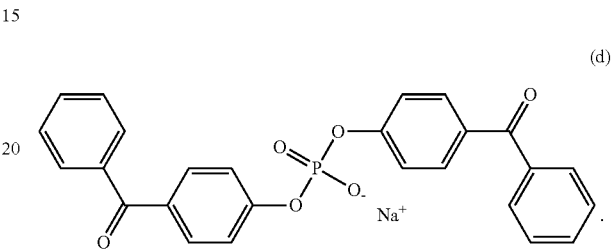

(d)

In a particular embodiment, the crosslinking agent can be bis(4-benzoylphenyl) phosphate.

In some embodiments, the photoactivatable crosslinking agent can be ionic, and can have good solubility in an aqueous composition, such as the first and/or second coating composition. Thus, in some embodiments, at least one ionic photoactivatable crosslinking agent is used to form the coating. In some cases, an ionic photoactivatable crosslinking agent can crosslink the polymers within the second coating layer which can also improve the durability of the coating.

Any suitable ionic photoactivatable crosslinking agent can be used. In some embodiments, the ionic photoactivatable crosslinking agent is a compound of formula I: X1-Y—X2 where Y is a radical containing at least one acidic group, basic group, or a salt of an acidic group or basic group. X1 and X2 are each independently a radical containing a latent photoreactive group. The photoreactive groups can be the same as those described herein. Spacers can also be part of X1 or X2 along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/mL. In some embodiments, the solubility is about 0.1 to about 10 mg/mL or about 1 to about 5 mg/mL.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; X1 and X2 can contain photoreactive groups such as aryl ketones.

Such compounds include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018 (to Swan). The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; X1 and X2 can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis (4-benzoylbenzyl)piperzinediium salt. See U.S. Pat. No. 5,714,360 (to Swan et al.). The counter ion is typically a carboxylate ion or a halide. On one embodiment, the halide is bromide.

In other embodiments, the ionic photoactivatable crosslinking agent can be a compound having the formula:

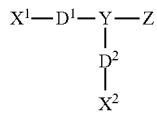

wherein X1 includes a first photoreactive group; X2 includes a second photoreactive group; Y includes a core molecule; Z includes at least one charged group; D1 includes a first degradable linker; and D2 includes a second degradable linker. Additional exemplary degradable ionic photoactivatable crosslinking agents are described in US Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula XR1R2R3R4, where X is a chemical backbone, and R1, R2, R3, and R4 are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

PG2-LE2-X-LE1-PG1 wherein PG1 and PG2 include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; LE1 and LE2 are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic crosslinking agents are described, for example, in Publ. No. U.S. 2012/0149934 (to Kurdyumov, "Photocrosslinker"), the disclosure of which is incorporated herein by reference.

Further embodiments of non-ionic photoactivatable crosslinking agents can include, for example, those described in US Pat. Publication 2013/0143056 (Swan et al., "Photo-Vinyl Linking Agents"), the disclosure of which is incorporated herein by reference. Exemplary crosslinking agents can include non-ionic photoactivatable crosslinking agents having the general formula R1-X—R2, wherein R1 is a radical comprising a vinyl group, X is a radical comprising from about one to about twenty carbon atoms, and R2 is a radical comprising a photoreactive group.

A single photoactivatable crosslinking agent or any combination of photoactivatable crosslinking agents can be used in forming a coating. In some embodiments, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis(4-benzoylbenzyldimethylammonium) salt or at least one anionic photoactivatable crosslinking agent such as 4,5-bis(4-benzoyl-phenylmethyleneoxy) benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Pat. No. 8,487,137 (to Guire et al.) and U.S. Pat. No. 7,772,393 (to Guire et al.) the contents of all of which is herein incorporated by reference.

In some embodiments, crosslinking agents can include boron-containing linking agents including, but not limited to, the boron-containing linking agents disclosed in U.S. Pat. No. 9,410,044 (to Kurdyumov) the content of which is herein incorporated by reference. By way of example, linking agents can include borate, borazine, or boronate groups and coatings and devices that incorporate such linking agents, along with related methods. In an embodiment, the linking agent includes a compound having the structure (I):

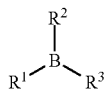 (I)

wherein R1 is a radical comprising a photoreactive group; R2 is selected from OH and a radical comprising a photoreactive group, an alkyl group and an aryl group; and R3 is selected from OH and a radical comprising a photoreactive group. In some embodiments the bonds B—R1, B—R2 and B—R3 can be chosen independently to be interrupted by a heteroatom, such as O, N, S, or mixtures thereof.

In some embodiments, the first coated layer comprises a cross-linking agent comprising at least two photoreactive groups, and amounts of the non-ionic polymer and a cross-linking agent comprising at least two photoreactive groups at a weight ratio in the range of about 2:1 to about 30:1 (wt./wt.), respectively. In some embodiments, in the first coated layer the amounts of non-ionic polymer (e.g., vinyl pyrrolidone polymer) and the cross-linking agent comprising at least two photoreactive groups are at a weight ratio in the range of about 2:1 to about 20:1 (wt./wt.), respectively, of about 8:1 to about 20:1 (wt./wt.), respectively, of about 8:1 to about 16:1 (wt./wt.), respectively, or about 18:1 (wt./wt.), respectively. In some embodiments, all components of the base coating comprise photoreactive groups.

In some embodiments, the first coated layer includes a non-ionic polymer without photoreactive groups (e.g., non-ionic, underivatized PVP). The underivatized non-ionic polymer (e.g., PVP) can be of various molecular weights. In some embodiments, the first coated layer has amounts of non-ionic polymer comprising a photoreactive group, non-derivatized non-ionic polymer, and cross-linking agent comprising at least two photoreactive groups at a weight ratio in the range of about 8:0.1:0.1 to 13:8:1 (wt./wt./wt.), respectively. In some embodiments, the first coated layer has amounts of non-ionic polymer comprising a photoreactive group, non-derivatized non-ionic polymer, and cross-linking agent comprising at least two photoreactive groups at a weight ratio of about 13:5:1 (wt./wt./wt.). In some embodiments, the first coated layer has amounts of non-derivatized non-ionic polymer and first cross-linking agent comprising at least two photoreactive groups at a weight ratio in the range of about 0.1:0.5 to 8:1 (wt./wt.), respectively.

In some embodiments, a coating solution is formed by including a non-ionic polymer (e.g., vinyl pyrrolidone polymer), optionally one or more other compounds, in a solvent. For example, the solvent can comprise a vinyl pyrrolidone polymer, having a pendent photoreactive group, or the solvent can comprise a non-derivatized vinyl pyrrolidone polymer and a cross-linking agent comprising at least two photoreactive groups. In some embodiments, the first coating solution can also include a mixture of a non-derivatized vinyl pyrrolidone polymer and a vinyl pyrrolidone polymer, having a pendent photoreactive group.

In some embodiments, the solvent for the first coating solution can include water and isopropyl alcohol (IPA). The proportion of IPA to water (vol:vol) can be in the range of about 95% IPA-5% water to about 10% IPA-90% water. For example, in some embodiments, the amount of IPA:water can a ratio of about 95:5, 90:10, 85:15, 80:20, 75:25, 70:30, 65:35, 60:40, 55:45, 50:50, 45:55, 40:60, 35:65, 30:70, 25:75, 20:80, 15:85, or 10:90 (vol:vol), or can be within a range with endpoints including any two of those ratios such that the total relative portions of IPA and water are equal to 100. In some embodiments, the solvent can include about 75% isopropyl alcohol and about 25% water.

The first coating solution can be applied to a substrate. Prior to application of the first coating solution to the substrate, one or more of many different pretreatment steps can be taken. In some embodiments, the surface of the substrate can be cleaned. For example, the surface can be wiped or dipped into an alcohol such as isopropyl alcohol. In some embodiments, the substrate can be put into a detergent solution such as a VALTRON solution and sonicated. In some embodiments, a compound can be disposed on the surface of the substrate to act as a tie layer. In some embodiments the surface of the substrate can be sterilized.

Many different techniques can be used to apply the solution to the substrate. By way of example, exemplary techniques can include drop coating, blade coating, dip coating, spray coating, and the like. In various embodiments, the solution is applied by dip coating. The speed of dip coating can vary. For example, the substrate can be dipped into the base coating solution and then withdrawn at speeds between 0.01 and 10 cm/s, between 0.1 and 4 cm/s, between 0.1 and 2 cm/s, between 0.1 and 1.5 cm/s, between 0.1 and 1 cm/s, between 0.1 and 0.5 cm/s, between 0.2 and 0.4 cm/s, or about 0.3 cm/s.

After the first coating solution is applied to the substrate, actinic radiation such as UV radiation, can be applied to activate photoreactive groups within the components of the first coating solution forming the base layer. Actinic radiation can be provided by any suitable light source that promotes activation of the photoreactive groups. Preferred light sources (such as those available from Dymax Corp.) provide UV irradiation in the range of 190 nm to 360 nm. An exemplary UV light source is a Dymax 2000-EC series UV flood lamp with a 400 Watt metal halide bulb. A suitable dose of radiation is in the range of about 0.5 mW/cm$^2$ to about 2.0 mW/cm$^2$. Optionally, the first coating solution can be dried, before or after application of the actinic radiation.

The drug delivery coating includes a second coated layer that includes an acid group-containing polymer, which is in contact with and is different than the first coated layer. Hydrogen bonding can exist between the first and second coated layer to provide improved coating properties. For example, the amide, ether, and/or alcohol group of the non-ionic polymer can hydrogen bond to the acid group of the acid polymer of the second coated layer.

An "acid group-containing polymer" refers to polymer that has acid groups presented on the polymer chain. Acidic groups include, for example, sulfonic acids, carboxylic acids, phosphonic acids, and the like. Exemplary salts of such groups include, for example, sulfonate, carboxylate, and phosphate salts. Exemplary counter ions include alkali, alkaline earths metals, ammonium, protonated amines, and the like. If one or more counter ions are used, the acid groups of the acid group-containing polymer are partially neutralized. For example a molar percentage of the acid groups can be neutralized with counter ions, such as in the range of x toy, wherein x toy are selected from about 1%, 5%, 10%, 15%, 20%, 25%, 30%, 40%, 50%, 60%, 70%, 80%, or 90%, wherein x is less than y.

Exemplary carboxylic acid-group containing monomers that can be used to prepare the acid group-containing polymer, include, but are not limited to acrylic acid, methacrylic acid, itaconic acid, monomethyl itaconic acid, maleic anhydride, fumaric acid, and crotonic acid, and salts thereof. Exemplary sulfonic acid-group containing monomers that can be used to prepare the acid group-containing polymer, include, but are not limited to acrylamido-2-methylpropanesulfonic acid (AMPS), 2-(meth)acrylamido-2-methylpropane sulfonic acid, vinyl sulfonic acid, 2-sulfoethyl methacrylate, and salts thereof. Copolymers made from a combination of two or more different acid-group containing monomers can be used, or copolymers made from one or more acid-group containing monomers and one or more non-acid group containing monomers can be used. These copolymers can be random copolymers, block copolymers, graft copolymers or blends thereof to achieve the desired outcome.

Other exemplary carboxylic acid-containing monomers that can be used to prepare the acid group-containing copolymers include styrene and maleic anhydride copolymerized to produce styrene-maleic anhydride copolymer (PSMA). Yet other exemplary carboxylic acid-containing monomers are described in "Hydrogen-Bonded Interpolymer Complexes; Formation, Structure and Applications" Chapters 1 and 7, Eds. Vitaliy V. Khutoryanskiy and Georgios Stalkos (2009).

The acid group-containing polymer may optionally be described with reference to its pH. For example, the acid group-containing polymer may have a pH in the range of about 1 to about 5, about 1.2 to about 5, about 1.5 to about 5, about 2.5 to about 5, about 2.75 to about 4.5, or about 3 to about 4.25.

In some embodiments, the second coated layer includes an acrylic acid polymer. As used herein an "acrylic acid polymer" refers to polymers including acrylic acid monomeric units. The acrylic acid polymer can be an acrylic acid homopolymer or an acrylic acid copolymer including acrylic acid and one or more (e.g., two, three, four, five, etc.) other monomeric units that are different than acrylic acid. In embodiments, in a poly(acrylic acid) copolymer, the acrylic acid can be the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater, 92.5% (mol) or greater, 95% (mol) or greater, 97.5% (mol) or 99% (mol) or greater. In exemplary embodiments, acrylic acid is present in the copolymer in the range of about 75% (mol) to about 100% (mol), about 85% (mol) to about 100% (mol), about 95% (mol) to about 100% (mol), or about 98% (mol) to about 100% (mol).

In some embodiments, the acrylic acid polymer in the second layer may have an average molecular weight of 150 kDa or greater, or an average molecular weight of 250 kDa or greater, 350 kDa, 450 kDa, 550 kDa, 650 kDa or greater or even in some cases an average molecular weight of 750 kDa or greater.

In embodiments, the acid group-containing polymer can be the predominant polymer(s) in the second coated layer (>50% wt of the total polymeric content of the second coated layer). Preferably, the acid group-containing polymer(s) is 75% wt or greater, 85% wt or greater, 90% wt or greater, 95% wt or greater, or 98% wt or greater, of the total polymeric content of the second coated layer. For example, the acid group-containing polymer is present in an amount in the range of about 50% wt to 100% wt, or 90% wt to 100% wt, of the total polymeric content of the second coated layer.

In some modes of preparation, the acrylic acid polymer is prepared by free radical polymerization of acrylic acid at (e.g., about a 0.8 M concentration) in deionized water. In modes where a portion of the acid groups are neutralized, a concentrated base such as NaOH is added to the acrylic acid solution. Next, an initiator such as ammonium persulfate is added with stirring. The polymerization solution can be degassed with nitrogen and stirred for hours (e.g., 12-24 hours) at an elevated temperature (e.g., greater than 50° C.). The polymer can then be polymerized against continuous flow deionized water using 12-14 K dialysis tubing, and then isolated by lyophilization.

Figure 6:
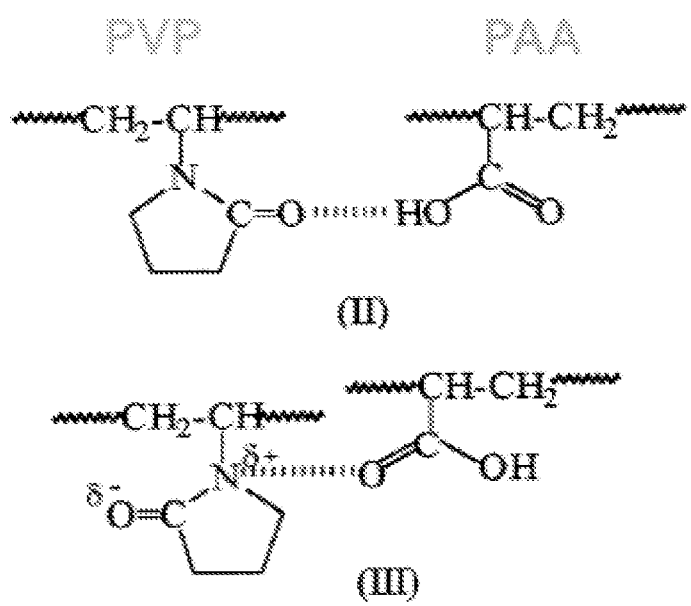
FIG. 6 is an illustration of hydrogen bonding between chemical groups of a vinyl pyrrolidone polymer (first coated layer) and acrylic acid polymer (second coated layer).

In exemplary embodiments, the drug delivery coating includes an acrylic acid polymer which undergoes hydrogen bonding with a vinyl pyrrolidone polymer of the first coated layer. More specifically, hydrogen bonding between the polymers can involve the carbonyl oxygens of both the pyrrolidone ring and the carboxylic acid, as shown in FIG. 6.

In other embodiments, the second coated layer also includes a cross-linking agent comprising at least two photoreactive groups, or an acrylamide polymer comprising at least one photoreactive group. The cross-linking agent may be the same or different than the cross-linking agent optionally used in the first coated layer. In some embodiments, the acrylamide polymer can comprise acrylamide, acrylamido-2-methylpropanesulfonate groups (AMPS), and poly(ethyleneglycol) groups. For example, in a specific embodiment, the acrylamide polymer can be N-acetylated poly[acrylamide-co-sodium-2-acrylamido-2-methylpropanesulfonate-co-N-(3-(4-benzoylbenzamido)propyl) methacrylamide]-co-methoxy poly(ethylene glycol) monomethacrylate. Reagents and method for the preparation of polymers comprising polyacrylamide in accordance with embodiments herein can be found in can be found in references such as U.S. Pat. Nos. 4,979,959; 5,002,582; 5,263,992; 5,414,075; 5,512,329; and 5,637,460, the teaching of which are incorporated herein by reference.

In some embodiments, some of the components of the second coated layer comprise photoreactive groups. In some embodiments, the second coated layer that is the top coating has amounts of acrylic acid polymer and acrylamide polymer at a ratio in the range of about 2:1 to about 1:2 (wt./wt.), respectively. In some embodiments, the second coated layer that is the top coating has amounts of acrylic acid polymer and second cross-linking agent comprising at least two photoreactive groups at a ratio of about 13:1 (wt./wt.). Within the second layer that is the top coating, the components can be homogenously mixed in some embodiments.

In some embodiments, the solvent for the second coating solution can include water and isopropyl alcohol (IPA). The proportion of IPA to water (vol:vol) can be in the range of 0% IPA-100% water to about 60% IPA-40% water. For example in some embodiments, the amount of IPA:water can be a ratio of about 0:100, 5:95, 10:90, 15:85, 20:80, 25:75, 30:70, 35:65, 40:60, 45:55, 50:50, 55:45, 60:40 (vol:vol), or can be within a range with endpoints including any two of those ratios such that the total relative portions of IPA and water are equal to 100. In some embodiments, the solvent can include about 15% isopropyl alcohol and about 85% water.

The second coating solution can be applied on top of the first coated layer. Many different techniques can be used to apply the solution to the substrate. In a particular embodiment, the solution is applied by dip coating. The speed of dip coating can vary. For example, the substrate can be dipped into the second coating solution and then withdrawn at speeds between 0.01 and 10 cm/s, between 0.1 and 4 cm/s, between 0.1 and 0.5 cm/s, between 0.2 and 0.4 cm/s, or about 0.3 cm/s.

In some embodiments, the combined thickness of the first layer (e.g., 104, 204, 304, 404, 504) and second layer (e.g., 106, 206, 306, 406, 506), can be in the range of about 100 nm to about 10.0 µm, about 250 nm to about 7.5 µm, or about 500 nm to about 5.0 µm. The coating can optionally be described in terms of the ratio of the thickness of the first coated layer to the second coated layer. For example, the ratio of the thickness can be in the range of about 50:1 to about 1:10 (first layer:second layer) (i.e., the first coated layer is about 50 times as thick as the second coated layer, or about one-tenth as thick as the second coated layer), about 20:1 to about 1:2, about 10:1 to about 1:1, or about 7.5:1 to about 2.5:1. In embodiments, the first coated layer is thicker than the second coated layer.

In some embodiments, the first and second layers are coated over both the balloon surface and the shaft of a balloon catheter. When used on the balloon shaft, the first and second layers, per se, can provide a highly lubricious surface to facilitate movement of the catheter in the vasculature. The coating exhibits lubricity that may be observed as relative low friction. The coating may exhibit lubricity of less than 30 grams of force, less than 20 grams of force, or less than 15 grams of force, when wetted as measured by a vertical pinch test. The coating can also exhibit very good durability as shown by tests wherein the lubricity is maintained over an extended period of time when the coating is exposed to frictional forces. For example, in some embodiments, lubricity may be maintained over a plurality of frictional testing cycles. In some embodiments, the coating may exhibit a lubricity of between 0 and 30 grams of force when wetted for at least 10 consecutive testing cycles. In some embodiments, such as where at least 15 frictional test cycles are performed, the measured lubricity will increase no more than 30% between the average of cycles 1-5 and the average of cycles 10-15 of the testing.

The coating may exhibit a relatively low amount of non-therapeutic agent non-degradable material particulate release (i.e., particulates otherwise formed as a byproduct of the first and/or second coated layers) when exposed to an aqueous environment. A description of particulate levels can be based on a predetermined coating area and thickness. In one mode of measurement the particle counts are based on 600 mm$^2$ of coated surface having a coating thickness in the range of 500 nm to 10 µm. However, it is understood that the particle count can be based on coating areas of greater or less than 600 mm$^2$. For example, the coating will generate less than 20,000 particles, less than 10,000 particles, less than 5,000 particles, less than 3,000 particles, or less than 1,000 particles of greater than 10 microns in size in an aqueous environment. In accordance with various embodiments herein, the properties of lubricity and low particulate release are both present.

Beneficially, in addition to the lubricity, durability, and low friction properties that the polymers of the first and second coated layers provide, these polymers also provide an excellent surface on which the particles of hydrophobic therapeutic agent and cationic agent can be disposed.

In addition to the first and second coated layers, the drug delivery coating includes particles of hydrophobic therapeutic agent and cationic agent. The particles of hydrophobic therapeutic agent and cationic agent can be associated with the coating in a variety of ways. For example, particles with cationic agent can be associated with the outer surface of the second coated layer as shown in FIG. 1; particles with cationic agent can be partially embedded and releasable from the second coated layer as shown in FIG. 2; particles with cationic agent can be embedded with the outer surface of an optional third coated layer as shown in FIG. 3, or associated with the outer surface of an optional third coated layer as shown in FIG. 4; particles within an optional third coated layer formed of cationic agent as shown in FIG. 5.

Hydrophobic active agents of embodiments herein (e.g., particle hydrophobic therapeutic agents), can include agents having many different types of activities. The terms "active agent" and "therapeutic agent" as used herein shall be coterminous unless the context dictates otherwise. Hydrophobic active agents can specifically include those having solubility in water of less than about 100 µg/mL at 25° C. and neutral pH. In various embodiments, hydrophobic active agents can specifically include those having solubility in water of less than about 10 µg/mL at 25° C. and neutral pH. In some embodiments, hydrophobic active agents can specifically include those having solubility in water of less than about 5 µg/ml at 25° C. and neutral pH.

In exemplary embodiments, active agents can include, but are not limited to, antiproliferatives such as paclitaxel, sirolimus (rapamycin), zotarolimus, everolimus, temsirolimus, pimecrolimus, tacrolimus, and ridaforolimus; analgesics and anti-inflammatory agents such as aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac; anti-arrhythmic agents such as amiodarone HCl, disopyramide, flecainide acetate, quinidine sulphate; anti-bacterial agents such as benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim; anti-coagulants such as dicoumarol, dipyridamole, nicoumalone, phenindione; anti-hypertensive agents such as amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL; anti-muscarinic agents: atropine, benzhexol HCl, biperiden, ethopropazine HCl, hyoscyamine, mepenzolate bromide, oxyphencylcimine HCl, tropicamide; anti-neoplastic agents and immunosuppressants such as aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone; beta-blockers such as acebutolol, alprenolol, atenolol, labetalol, metoprolol, nadolol, oxprenolol, pindolol, propranolol; cardiac inotropic agents such as amrinone, digitoxin, digoxin, enoximone, lanatoside C, medigoxin; corticosteroids such as beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone; lipid regulating agents such as bezafibrate, clofibrate, fenofibrate, gemfibrozil, probucol; nitrates and other anti-anginal agents such as amyl nitrate, glyceryl trinitrate, isosorbide dinitrate, isosorbide mononitrate, pentaerythritol tetranitrate.

Other exemplary embodiments of active agents include, but are not limited to, active agents for treatment of hypertension (HTN), such as guanethidine.

In a particular embodiment, the hydrophobic active agents are selected from the group consisting of paclitaxel, sirolimus (rapamycin) and mixtures thereof.

Particles that include hydrophobic therapeutic agent, and which are releasable from the drug delivery coatings of the disclosure can be of any desired shape and size and composition. The particles can be any three-dimensional particle having a size (e.g., an average diameter ("dn", number average) in the range of about 100 nm to about 20 µm, about 100 nm to about 10 µm, about 150 nm to about 7.5 µm, about 250 nm to about 5 µm, or about 500 nm to about 5 µm. The particles can also be of any shape (spherical, or substantially spherical, non-spherical shapes or irregular shape, such as rod-like, filament-like, sliver-like, or needle-like shapes) sufficient to be associated with the coatings of the disclosure and then released to a target tissue. Particle size and size distribution of a particle preparation can be determined by laser diffraction.

Exemplary particle hydrophobic therapeutic agents can have different morphological characteristics. In some embodiments the hydrophobic therapeutic agent particle can be crystalline. In yet other embodiments of the present disclosure the hydrophobic therapeutic agent particle can be amorphous. Additionally, combinations of crystalline and amorphous hydrophobic therapeutic agent particles can be desirable in order to achieve, for example, desired solubilities of the hydrophobic therapeutic agent.

Particles can include biocompatible materials that incorporate and/or encapsulate the hydrophobic therapeutic agent. These biocompatible materials can be biodegradable polymers (PLA, PLGA, etc.), (semi) solid lipids, biosilica, etc.

Particles that are predominately or solely of one or more hydrophobic therapeutic agent can be associated with the coating and released to target tissue in vivo. In other words, the particles can be formed substantially or entirely of one or more hydrophobic therapeutic agent, and an excipient substance that may otherwise control release of the hydrophobic therapeutic agent from the particle is not required. A particle that is formed entirely or almost entirely (e.g., allowing for trace amounts of one or more other components) of a bioactive agent may be referred to herein as a "neat" particle. The bioactive agent can be in amorphous form, in crystalline form or any mixture thereof.

For example, the preparation of paclitaxel microparticles has been described in U.S. Pat. No. 6,610,317. U.S. Pat. No. 9,439,892 (Slager) describes macrolide (e.g., rapamycin) particles including macrolide therapeutic agent in an amount of 95% or greater of the weight of the particle and a component selected from the group consisting of polyoxyethylene sorbitan n-acyl esters, poly(alkyleneimines), alkylated quaternary ammonium salts, and alkyl-substituted chromanols. The particles have a spherical or substantially spherical substantially spherical shape and a diameter in the range 0.1 µm to 10 µm. U.S. Publication No. 2015/0017219 describes macrolide (e.g., rapamycin) particles having a size of about 20 µm or less, or about 10 µm or less, such as in the range of 500 nm to 10 µm, wherein the macrolide is in crystalline form. The '219 publication describes various methods, including unique combinations of solvents and/or processing steps, to prepare these macrolide particles in crystalline form that have desirable sizes.

A composition that includes therapeutic agent particles can be applied to the second coated layer that includes the acid polymer. The composition can include a liquid carrier that maintains the integrity of the particles and the activity of the therapeutic agent. In an embodiment, a composition of water, or buffer water, and particles is applied to the second coated layer. The composition and method of disposing can provide a desired amount of therapeutic agent in the coating.

For example, in one embodiment, an amount of sirolimus (rapamycin) per area of balloon surface is in the range of about 0.5 µg/mm$^2$ to about 10 µg/mm$^2$ is used, such as about 5 µg/mm$^2$ per area (approximately 660 µg paclitaxel per balloon). The particles can be applied by any suitable dispensing means, such as a positive displacement pipette, and dried. If the particles are not associated with a cationic agent upon application, the cationic agent can be added after the particles are applied to the second coated layer.

In some embodiments, the hydrophobic therapeutic agent is be conjugated to a cationic agent. The conjugation can include a hydrophobic active agent covalently bonded to the cationic agent. In some embodiments wherein the hydrophobic agent is conjugated to the cationic agent a linking agent can be used to attach the hydrophobic agent to the cationic agent. Suitable linking agents include, but are not limited to, polyethylene glycol, polyethylene oxide and polypeptides of naturally-occurring and non-naturally occurring amino acids. In some embodiments, linking agents can be biodegradable or cleavable in vivo to assist in release of the hydrophobic active agents. Exemplary linking agents can further include alkane or aromatic compounds with heteroatom-substitutions such as N, S, Si, Se or O.

Cationic agents used in embodiments herein can include compounds containing a portion having a positive charge in aqueous solution at neutral pH along with a portion that can exhibit affinity for hydrophobic surfaces (such as hydrophobic or amphiphilic properties) and can therefore interface with hydrophobic active agents. In some embodiments, cationic agents used in embodiments herein can include those having the general formula X—Y, wherein X is a radical including a positively charged group in aqueous solution at neutral pH and Y is a radical exhibiting hydrophobic properties. In some embodiments, the cationic agent can include a hydrophilic head and a hydrophobic tail, along with one or more positively charged groups, typically in the area of the hydrophilic head.

Cationic agents of the present disclosure can include salts of cationic agents at various pH ranges, such as, but not limited to, halide salts, sulfate salts, carbonate salts, nitrate salts, phosphate salts, acetate salts and mixtures thereof.

Cationic agents can specifically include cationic lipids and net neutral lipids that have a cationic group (neutral lipids with cationic groups). Exemplary lipids can include, but are not limited to, 3ß-[N—(N',N'-dimethylaminoethane)-carbamoyl]cholesterol hydrochloride (DC-cholesterol); 1,2-dioleoyl-3-trimethylammonium-propane (DO-TAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethylammonium-propane (DODAP); 1,2-dilinoleyloxy-3-dimethylaminopropane (DLinDMA) and derivatives thereof. Additional lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE).Other cationic agents can include mono- or polyaminoalkanes such as spermine and spermidine.

Cationic agents can specifically include cationic polymers. Cationic agents can also include polycation-containing cyclodextrin (for example, but not limited to, amino cyclodextrin and derivatives thereof), amino dextran, histones, protamines, cationized human serum albumin, aminopolysaccharides such as chitosan, peptides such as poly-L-lysine, poly-L-ornithine, and poly(4-hydroxy-L-proline ester, and polyamines such as polyethylenimine (PEI; available from Sigma Aldrich), polyallylamine, polypropylenimine, polyamidoamine dendrimers (PAMAM; available from Sigma Aldrich), cationic polyoxazoline and poly(beta-aminoesters). Cationic agents can also specifically include cationic lipidoids (as described by K. T. Love in the publication PNAS 107, 1864-1869 (2010)). Other exemplary cationic polymers include, but are not limited to, block copolymers such as PEG-PEI and PLGA-PEI copolymers.

Other exemplary cationic agents include positively charged gelatin (for example, base-treated gelatin), and the family of aminated cucurbit[n]urils (wherein n=5, 6, 7, 8, 10).

In other embodiments of the present disclosure, cationic agents containing a portion having a positive charge in aqueous solutions at neutral pH include the following Compounds (A-I):

Compound A
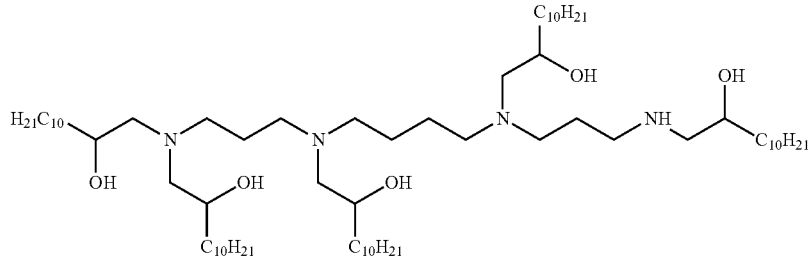

Compound B
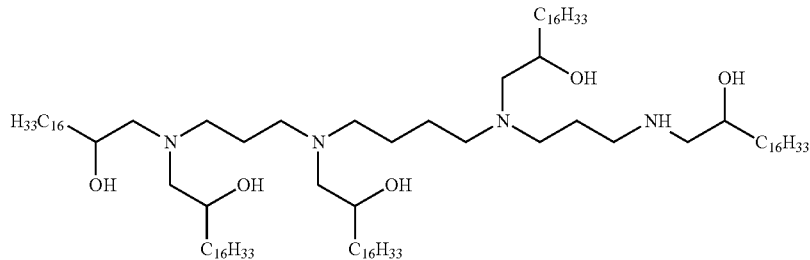

Compound C
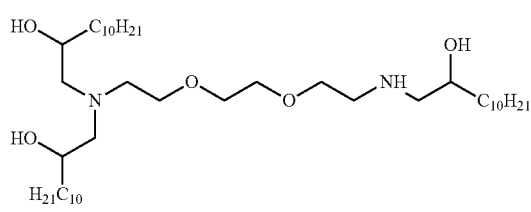

Compound D
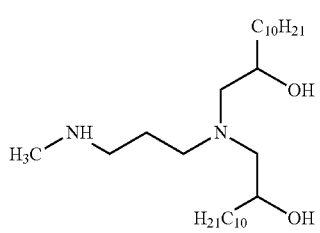

Compound E
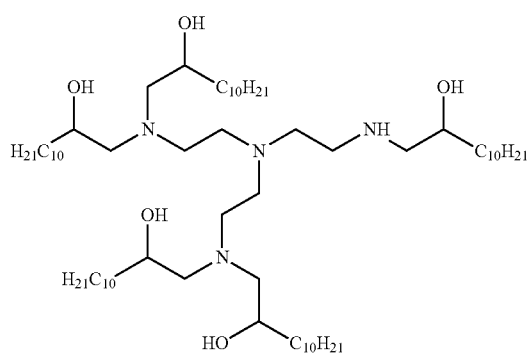

Compound F
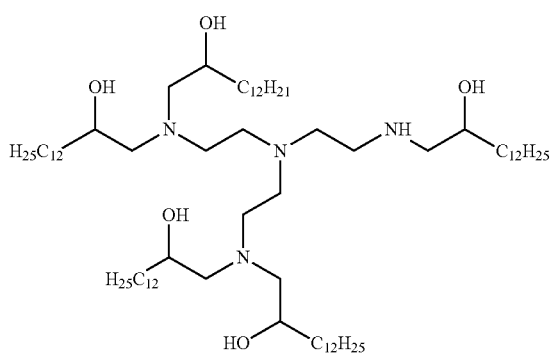

-continued

Compound G

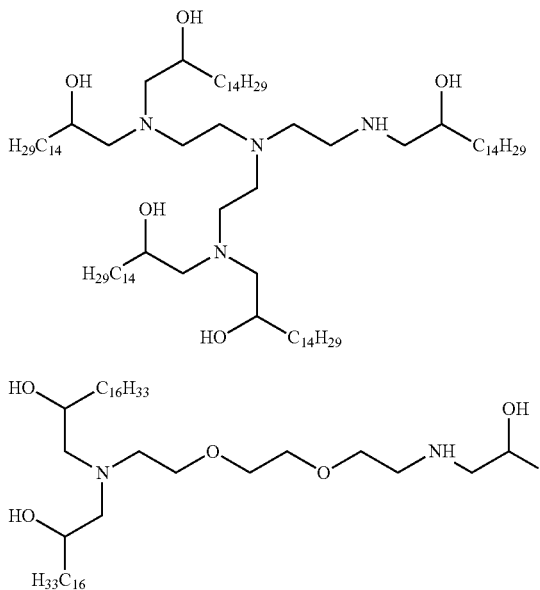

Compound H

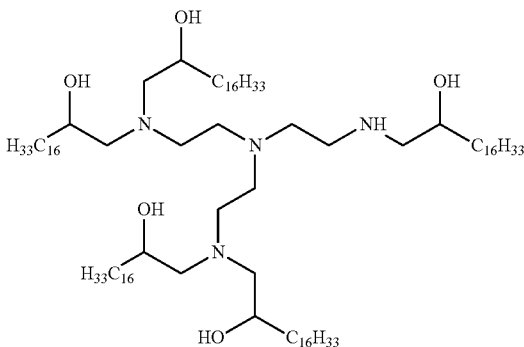

Compound I

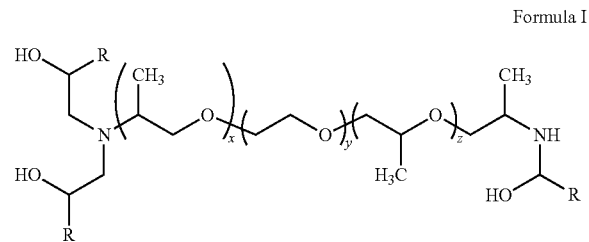

Additionally, other cationic agents include structures of the general Formula I:

Formula I

HO—R, CH₃, CH₃, NH, HO—R (structure of Formula I)

TABLE 1

Values for Variables x + z, y and R for Compounds J-R of Formula I.

| Compound | x + z | y | R |
|---|---|---|---|
| Compound J | 6 | 12.5 | $C_{12}H_{25}$ |
| Compound K | 1.2 | 2 | $C_{12}H_{25}$ |
| Compound L | 6 | 39 | $C_{12}H_{25}$ |
| Compound M | 6 | 12.5 | $C_{14}H_{29}$ |
| Compound N | 1.2 | 2 | $C_{14}H_{29}$ |
| Compound O | 6 | 39 | $C_{14}H_{29}$ |
| Compound P | 6 | 12.5 | $C_{16}H_{33}$ |
| Compound Q | 1.2 | 2 | $C_{16}H_{33}$ |
| Compound R | 6 | 39 | $C_{16}H_{33}$ |

Cationic agents, such as those listed above, can generally be prepared by the reaction of an appropriate hydrophobic epoxide (e.g. oleyl epoxide) with a multi-functional amine (e.g. propylene diamine). Details of the synthesis of related cationic agents are described by K. T. Love in the publication PNAS 107, 1864-1869 (2010) and Ghonaim et al., Pharma Res 27, 17-29 (2010).

It will be appreciated that polyamide derivatives of PEI (PEI-amides) can also be applied as cationic agents. PEI-amides can generally be prepared by reacting PEI with an acid or acid derivative such as an acid chloride or an ester to form various PEI-amides. For example, PEI can be reacted with methyl oleate to form PEI-amides.

In yet other embodiments cationic agents can include moieties used to condense nucleic acids (for example lipids, peptides and other cationic polymers). In some instances these cationic agents can be used to form lipoplexes and polyplexes.

Exemplary embodiments of cationic agents can also include, but are not limited to, cationic agent derivatives that are photo reactive. Photo reactive groups are described below. Such cationic agent derivatives include PEI polymer derivatives of benzophenone and PAMAM polymer derivatives of benzophenone.

In some embodiments, the molecular weight of the cationic agent can be about 1.2 kDa, 2.5 kDa, 10 kDa, 25 kDa, 250 kDa or even, in some cases, 750 kDa. In yet other embodiments the molecular weight of the cationic agent can be in the range of 50-100 kDa, 70-100 kDa, 50-250 kDa, 25-100 kDa, 2.5-750 kDa or even, in some cases, 2.5-2,000 kDa. Other embodiments include molecular weights greater than 1.2 kDa, 2.5 kDa, 10 kDa, 25 kDa, 250 kDa or even, in some cases, greater than 750 kDa. Other embodiments can include cationic agents up to 2,000 kDa.

Low molecular weight cationic agent monomers or low molecular weight cationic oligomers can be combined with hydrophobic active agent to produce a reactive coating. These reactive coatings can then be coated onto a substrate and thermally polymerized or polymerized with UV-radiation. Exemplary monomers include, but are not limited to, aziridine, vinylamine, allylamine and oligomers from 80 g/mol to 1200 g/mol. Crosslinkers (e.g., 1,2-dichloroethane, epichlorohydrin, 1,6-diisocyanatohexane) could be used to crosslink oligomers.

In some embodiments, nucleic acids may also be included in the drug delivery coatings of the disclosure. By way of example, nucleic acids, including but not limited to siRNA, may be associated with the cationic agent. Exemplary nucleic acids are described in greater detail below. The coated therapeutic agent particles can include a plurality of cationic agents disposed over a hydrophobic therapeutic agent particle and nucleic acids can be associated with the cationic agent. The charge provided by the cationic agents can be electrostatically attracted to negative charges and/or polar groups associated with the lipid bilayer of a cell membrane and cellular components within the lipid bilayer.

Nucleic acids used with embodiments of the invention can include various types of nucleic acids that can function to provide a therapeutic effect. Exemplary types of nucleic acids can include, but are not limited to, ribonucleic acids (RNA), deoxyribonucleic acids (DNA), small interfering RNA (siRNA), micro RNA (miRNA), piwi-interacting RNA (piRNA), short hairpin RNA (shRNA), antisense nucleic acids, aptamers, ribozymes, locked nucleic acids and catalytic DNA. In a particular embodiment, the nucleic acid used is siRNA and/or derivatives thereof.

In some exemplary embodiments of the present disclosure, the range of the percent ratio of hydrophobic active agent to cationic agent (e.g. % PTX/% PEI or % PTX/% DOTAP; wt/wt) is from about 99.9/0.1 to about 70/30. In yet other embodiments it can be appreciated that the range of the percent ratio of hydrophobic active agents is from about 99/1 to about 73/27; from about 98/2 to about 75/25; from about 98/2 to about 86/14; from about 97/3 to about 88/12; from about 95/5 to about 90/10; and even in some exemplary embodiments from about 93/7 to about 91/9.

A composition of hydrophobic active agent particles and cation agent in a liquid carrier, such as ethanol, can be prepared and the composition can be applied to the surface of the second coated layer. The particles and cationic agent can be applied by any suitable dispensing means, such as a positive displacement pipette, and dried.

Optionally, the drug delivery coating can include a third coated layer that is in contact with the second coated layer. Such an optional layer can provide benefits for the delivery of the therapeutic agent particle, or can protect the particle prior to the therapeutic agent being released to tissue. If a third coated layer in contact with the second coated layer is present, the therapeutic agent particle can be located within the third coated layer (such as shown in FIG. 3), the therapeutic agent particle can be between the second and third coated layer (such as a top coat over the particles), or the therapeutic agent particle can be associated with the surface of the third coated layer (such as shown in FIG. 4). An optional third coated layer can be less stable than the first and second coated layer, and can include one or more biodegradable materials, or biocompatible materials that loosen from the drug coating and is partially or fully removed during the drug delivery method. Materials of the optional third layer can modify the release characteristic of the hydrophobic active agent.

In some embodiments, the cationic agent, as described herein, is applied to the second coated layer to form a third coated layer. The hydrophobic therapeutic agent particles can be partially or fully within a third coated layer formed from the cationic agent.

Exemplary biodegradable material that can be used in the drug delivery coating includes biodegradable polymers that can be broken down by various enzymes, such as those in the normal functioning of the human body and living organisms (such as bacteria) and/or in water environments (by simple hydrolysis). Degradable polymers can be natural or synthetic, or can be composed of natural and synthetic blocks.

In some modes of practice, the degradable polymer is synthetic. Exemplary synthetic degradable polymers can be selected from the group of polyesters such as poly(lactic acid) (poly(lactide)), poly(glycolic acid) (poly(glycolide)) poly(lactide-co-glycolide), poly(dioxanone); polylactones such as poly(caprolactone) and poly(valerolactone), copolymers such as poly(glycolide-co-polydioxanone), poly(glycolide-co-trimethylene carbonate), and poly(glycolide-co-caprolactone); poly(3-hydroxybutyrate), poly(3-hydroxyvalerate), poly(tartronic acid), poly(β-malonic acid), polypropylene fumarate); degradable polyesteramides; degradable polyanhydrides and polyalkeneanhydrides (such as poly(sebacic acid), poly(1,6-bis(carboxyphenoxy)hexane, poly(1,3-bis(carboxyphenoxy)propane); degradable polycarbonates and aliphatic carbonates; degradable polyiminocarbonates; degradable polyarylates; degradable polyorthoesters; degradable polyurethanes; degradable polyphosphazenes; degradable polyhydroxyalkanoates; and degradable polyamides.

In other embodiments, the optional third coated layer includes a biocompatible lipid which can loosen from the drug coating and can facilitate delivery of the therapeutic agent particles. The lipid composition can include a single lipid or mixture of lipids. The lipid or mixture of lipids can, for example, be solid (e.g., waxy or paste-like) or semi-solid at room temperature and soft or liquid at the body temperature of a subject. In an embodiment, the lipid composition includes a first lipid with a melting point at or above 40° C., at or above 37° C., or in the range about 35° C. to about 45° C., and a second lipid with a melting point at or below 30° C., at or below 25° C., such as in the range of about 0° C. to about 35° C. Exemplary lipids are from animals or vegetable, and include fatty acids. An exemplary fatty acid mixture is oleic acid and dodecanoic acid.

In other embodiments, the optional third coated layer can include a saccharide. Saccharides can include monosaccharides, disaccharides, trisaccharides, oligosaccharides, and polysaccharides, and derivatives of polysaccharides. Polysaccharides can be linear or branched polysaccharides. Exemplary saccharides can include but are not limited to dextrose, sucrose, maltose, mannose, trehalose, and the like. Exemplary saccharides can further include, but are not limited to, polysaccharides including pentose, and/or hexose subunits, specifically including glucans such as glycogen and amylopectin, and dextrins including maltodextrins, fructose, mannose, galactose, and the like. Polysaccharides can also include gums such as pullulan, arabinose, galactan, etc.

In other embodiments, the optional third coated layer can include an amphiphilic compound. Amphiphilic compounds include those having a relatively hydrophobic portion and a relatively hydrophilic portion. Exemplary amphiphilic compounds can include, but are not limited to, polymers including, at least blocks of, polyvinyl-pyrrolidone, polyvinyl alcohol, polyethylene glycol, polyoxazolines (such as poly (2-alkyloxazoline) and derivatives) and the like. Exemplary amphiphilic compounds can specifically include poloxamers. Poloxamers are nonionic triblock copolymers composed of a central hydrophobic chain of polyoxypropylene flanked by two hydrophilic chains of polyoxyethylene. Poloxamers are frequently referred to by the trade name PLUIRONIC®.

In other embodiments, the optional third coated layer can include a compound that stabilizes the hydrophobic therapeutic agents. Exemplary additive components providing such stabilization include biocompatible polymers, for example albumins. Additional additive components are described in U.S. Pat. No. 7,034,765 (De et al.), the disclosure of which is incorporated herein by reference. Stabilization of suspensions and emulsions can also be provided by compounds, for example, such as surfactants (e.g. F68).

In exemplary embodiments, the drug delivery coating is formed on the balloon surface of a balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guidewire, and manifold. A balloon catheter generally includes an elongated catheter shaft with the inflatable balloon attached to a distal section of the catheter shaft. At a proximal end of the catheter shaft, there is typically a manifold. At the manifold end, placement of the catheter can be facilitated using a guidewire. Guidewires are small and maneuverable when inserted into an artery. Once the guidewire is moved to the target location, the catheter with balloon portion is then fed over the guidewire until the balloon reaches the target location in the vessel. The balloon is then inflated when the catheter reaches the targeted constriction to thereby apply the requisite mechanical force to cause vessel dilation. The manifold can also control the fluid introduction within shaft for expansion of the balloon. The balloon is typically inserted into the arterial lumen of a patient and advanced through the lumen in an unexpanded state.

Prior to inflation the balloon can be folded to a compacted configuration for delivery to the target site. A folding process may involve creating "arms" of the balloon material and folding these arms inward (towards the catheter axis) to compact the balloon material.

The balloon catheter can be used in a kit or system along with a balloon catheter introducer tool. Examples of such tools are described in commonly assigned PCT application WO 2016/115361 (Jelle, et al., published Jul. 21, 2016) and U.S. Application No. 62/395,610 (Trocke, et al., Sep. 16, 2016).

The balloon is typically inflated using a fluid, which is injected through an inflation port. The mechanics of fluid transfer and introduction within balloons vary according to the specific design of the catheter, and are well known in the art.

A balloon catheter with the drug delivery coating of the disclosure can be used in a balloon angioplasty procedure. Balloon angioplasty is commonly carried out for the treatment of diseased arteries to reduce atherosclerotic stenosis or to recanalize occluded arteries. In such a procedure, obstructed intraluminal passages are reopened or dilated by inflation of the balloon at the occluded site. According to the invention, balloon catheter having balloon portion with the drug delivery coating is inserted percutaneously into a luminal passage of a patient, such as an artery, vein, or airway. Once inserted, the balloon is advanced to the desired treatment site, where the balloon is inflated to dilate the luminal passage. The drug delivery coating of the disclosure can minimize or eliminate hydrophobic therapeutic agent loss prior to placing the coated balloon portion at the treatment site.

Upon inflation of the balloon, particles and cationic agent are associated with the surface of the balloon can be transferred to the tissue of lumenal arterial wall at the target site. In some modes of delivery, inflation of the balloon stretches the coating which can undergo physical changes that promote the release of the particles. The first and second coated layers can also become more hydrated which can also facilitate particle release.

One beneficial aspect of various embodiments described herein is that the therapeutic agent can be transferred from the drug delivery device or coating to the targeted tissue very rapidly. In some embodiments substantial transfer of the therapeutic agent from the drug delivery coating to the tissue occurs in 30 minutes or less. In some embodiments substantial transfer of the therapeutic agent from the drug delivery device or coating to the tissue occurs in 15 minutes or less. In some embodiments substantial transfer of the therapeutic agent from the drug delivery device or coating to the tissue occurs in 10 minutes or less. In some embodiments substantial transfer of the therapeutic agent from the drug delivery device or coating to the tissue occurs in 5 minutes or less. In some embodiments substantial transfer of the therapeutic agent from the drug delivery device or coating to the tissue occurs in 2 minutes or less. In some embodiments substantial transfer of the therapeutic agent from the drug delivery device or coating to the tissue occurs in 1 minute or less.

The particles with cationic agent that are transferred can associate with tissue at the target site and the particles can release therapeutic agent to provide a therapeutic effect on the tissue. The release of the therapeutic agent at the target site can be useful to control tissue response after balloon dilation. For example, the particles can release an antiproliferative agent, such as sirolimus or paclitaxel that can inhibit neointimal proliferation at the dilated site.

In some aspects, particles can be used to release bioactive agent at the target site in a sustained profile. This feature allows for release of the therapeutic agent from the particles over a longer and more therapeutically useful time period.

What is claimed is:

1. A device having a drug delivery coating comprising
(a) a first coated layer comprising (a1) a non-ionic polymer comprising one or more chemical groups selected from the group consisting of amides, ethers, and alcohols, and (a2) photoreactive groups, wherein the photoreactive groups are pendent from the non-ionic polymer or, when present, from a cross-linking agent, wherein the cross-linking agent comprises at least two photoreactive groups, or both;
(b) a second coated layer that is in direct contact with the first coated layer, the second coated layer comprising an acid polymer, wherein the first coated layer is between the second coated layer and a device surface, and wherein the acid polymer is present in the second coated layer in an amount greater than 90% (wt) of a total polymeric content of the second coated layer;
(c) a particle comprising a hydrophobic therapeutic agent; and
(d) a cationic agent;
wherein the cationic agent is associated with the particle, and the particle is within the second coated layer, associated with an outer surface of the second coated layer, or associated with an optional coated layer that is outer to the second coated layer, wherein the device surface to the second coated layer represents an inner to outer direction, respectively.

2. The device of claim 1 wherein the non-ionic polymer comprises an amide group that is a tertiary amide group, or the non-ionic polymer, comprises an amide group that is part of a lactam group.

3. The device of claim 1 wherein the acid polymer in the second coated layer is an acrylic acid polymer.

4. The device of claim 1 wherein the particle comprising the hydrophobic therapeutic agent and the cationic agent form coated therapeutic agent particles.

5. The device of claim 1 comprising a material on which the drug delivery coating is formed, wherein the material is selected from the group consisting of polyamide, polyimide, polyether block amide (PEBAX), polyether ether ketone (PEEK), high density polyethylene (HDPE), polyethylene, polyurethane, polyethylene vinyl acetate, polyethylene, styrene-butadiene copolymers, polyisoprene, isobutylene-isoprene copolymers (butyl rubber), butadiene-styrene-acrylonitrile copolymers, silicone polymers, fluorosilicone polymers, polycarbonates, polyesters, polyvinyl chloride, polyether-polyester copolymers, and polyether-polyamide copolymers.

6. The device of claim 1 comprising a catheter.

7. The device of claim 1 wherein the drug delivery coating is formed on a balloon surface of a balloon catheter.

8. The device of claim 1 wherein the non-ionic polymer is selected from the groups consisting of poly(N-vinyl caprolactam), poly-(vinyl pyrrolidone), poly(vinyl methyl ether), polyacrylamide, poly(N-isopropylacrylamide), poly(N,N-dimethylacrylamide), poly(vinyl alcohol) (PVA), poly(2-hydroxyethyl vinyl ether) PHEVE), poly(2-ethyl-2-oxazoline) (PEOX), poly(n-acetyliminoethylene) (PAIE), methyl cellulose, hydroxypropylcellulose, and hydroxyethylcellulose.

9. The device of claim 1 wherein the acid polymer is present in the second coated layer in an amount greater than 95% (wt) of the total polymeric content of the second coated layer.

10. The device of claim 1 wherein the particle is within the second coated layer or associated with an outer surface of the second coated layer.

11. The device of claim 1 wherein the non-ionic polymer is a vinyl pyrrolidone polymer.

12. The device of claim 11 wherein the vinyl pyrrolidone polymer comprises pendent photoreactive groups.

13. The device of claim 1 wherein first coated layer comprises a crosslinking agent comprising pendent photoreactive groups.

14. The device of claim 13 wherein the crosslinking agent is selected from the group consisting of:

(a)

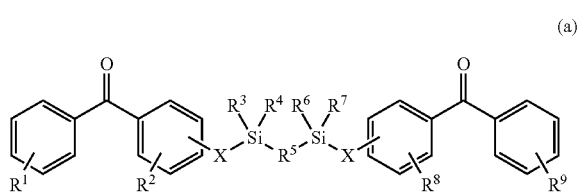

wherein $R^1$, $R^2$, $R^8$ and $R^9$ are any substitution; $R^3$, $R^4$, $R^6$ and $R^7$ are alkyl, aryl, or a combination thereof; $R^5$ is any substitution; and each X, independently, is O, N, Se, S, or alkyl, or a combination thereof;

(b)

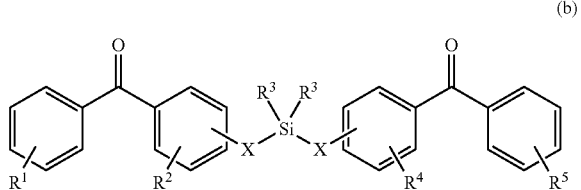

wherein $R^1$ and $R^5$ are any substitution; $R^2$ and $R^4$ can be any substitution, except OH; $R^3$ can be alkyl, aryl, or a combination thereof; and each X, independently, is O, N, Se, S, alkyl or a combination thereof;

(c)

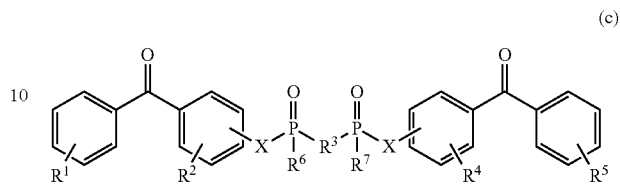

wherein $R^1$, $R^2$, $R^4$ and $R^5$ are any substitution; $R^3$ is any substitution; $R^6$ and $R^7$ are alkyl, aryl, or a combination thereof; and each X, independently, is O, N, Se, S, alkyl, or a combination thereof; and (d)

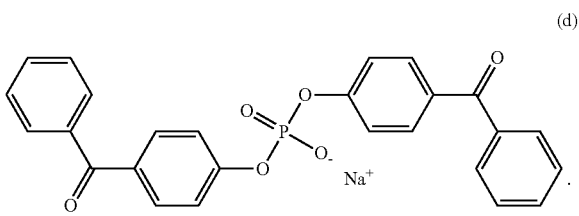

15. The coating of claim 14 wherein the cross-linking agent(s) is sodium bis(4-benzoylphenyl) phosphate.

16. The device of claim 1 wherein the hydrophobic therapeutic agent is a macrolide or a taxane.

17. The device of claim 16 wherein the macrolide is selected from the group consisting of rapamycin, everolimus, pimecrolimus, temsirolimus, tacrolimus, deforolimus, zotarolimus, and biolimus.

18. The device of claim 1 wherein the cationic agent is selected from the group consisting of cationic lipids, neutral lipids with cationic groups, and cationic polymers.

19. The device of claim 18 wherein the cationic agent is selected from the group consisting of polyethyleneimine and 1,2-dioleoyl-3-trimethylammonium-propane (DOTAP).

20. The device of claim 1 wherein the non-ionic polymer is present in an amount of 75% wt or greater of a total polymeric content of the first coated layer.

21. The device of claim 20 wherein the non-ionic polymer is present in an amount in the range of 90% wt to 100% wt of the total polymeric content of the first coated layer.

22. A method for providing a therapeutic agent to a subject comprising inserting the device of claim 1 into the subject that is a patient, wherein the therapeutic agent is released to the patient to provide a therapeutic effect.

\* \* \* \* \*